(12) United States Patent
Robinson et al.

(10) Patent No.: US 6,771,172 B1
(45) Date of Patent: Aug. 3, 2004

(54) PORTABLE PATIENT MONITOR WITH ALARM LIGHT INTEGRATED INTO HANDLE

(75) Inventors: Scott W. Robinson, Bayside, WI (US); Eric R. Slotty, Waukesha, WI (US); Alan E. Clapp, Milwaukee, WI (US); Patrick Allen Van Ryzin, Pewaukee, WI (US); Richard J. Frangesch, Elm Grove, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/438,756

(22) Filed: Nov. 11, 1999

(51) Int. Cl.$^7$ ................................................ G08B 23/00
(52) U.S. Cl. .................. 340/573.1; 340/321; 340/691.1; 16/110.1; 16/436; 40/661.12; 294/137; 600/301; 600/523; 600/554; 362/399
(58) Field of Search .......................... 340/573.1, 691.1, 340/321, 870.01, 870.16; 169/110.1, 436, 438; 294/137; 40/661.12; 600/554, 301, 587, 509, 523; 607/1, 58, 72, 156, 150; 362/399

(56) References Cited

U.S. PATENT DOCUMENTS

| | | | | |
|---|---|---|---|---|
| 2,165,343 A | | 7/1939 | Cole .......................... 177/311 |
| 3,761,920 A | * | 9/1973 | Houbolt et al. .......... 340/815.5 |
| 4,312,361 A | * | 1/1982 | Nicholson et al. .......... 600/651 |
| 4,350,164 A | | 9/1982 | Allain, Jr. .................... 128/639 |
| 4,399,631 A | * | 8/1983 | Smith ............................. 43/17 |
| 4,605,882 A | | 8/1986 | DeLuca ....................... 315/158 |
| 4,653,474 A | * | 3/1987 | Reithler .......................... 607/5 |
| 4,775,920 A | * | 10/1988 | Seibert et al. .............. 362/109 |
| 4,795,873 A | * | 1/1989 | Freedman et al. .......... 219/728 |
| 4,800,878 A | | 1/1989 | Cartmell ................ 128/303.14 |
| 4,895,161 A | * | 1/1990 | Cudahy et al. ............. 600/523 |
| 5,031,629 A | * | 7/1991 | DeMarzo ..................... 600/483 |
| 5,099,401 A | * | 3/1992 | Kondo et al. ............... 362/541 |
| 5,131,401 A | * | 7/1992 | Westenskow et al. ....... 600/554 |
| 5,160,200 A | * | 11/1992 | Cheselske ................... 362/249 |
| 5,297,010 A | * | 3/1994 | Camarota et al. ............. 362/80 |
| 5,408,395 A | * | 4/1995 | Schmid et al. ............. 362/240 |
| 5,488,537 A | * | 1/1996 | Heald et al. ................. 361/684 |
| 5,512,057 A | * | 4/1996 | Reiss et al. ................... 600/67 |
| 5,521,812 A | * | 5/1996 | Feder et al. .................. 700/90 |
| 5,649,759 A | * | 7/1997 | Korte ......................... 362/226 |
| 5,711,302 A | * | 1/1998 | Lampropoulos et al. .... 600/485 |
| 5,764,034 A | * | 6/1998 | Bowman et al. ............ 320/155 |
| 5,785,528 A | * | 7/1998 | Jones-Fenleigh et al. ..... 434/88 |
| 5,896,093 A | * | 4/1999 | Sjobom ................. 340/815.75 |

(List continued on next page.)

FOREIGN PATENT DOCUMENTS

| | | |
|---|---|---|
| DE | 29910417 | 8/1999 |
| EP | 0231987 | 8/1987 |
| EP | 0767269 | 4/1997 |
| GB | 698929 | 10/1953 |

*Primary Examiner*—Davetta W. Goins
(74) *Attorney, Agent, or Firm*—Ostrager Chong & Flaherty LLP

(57) ABSTRACT

An alarm light integrated into the top of the handle of a portable patient monitor or other portable medical diagnostic instrument. Since the top of the handle is the highest point of the monitor, the alarm light can be clearly seen from the sides, top and back of the monitor. Because the alarm light is integrated into the handle structure, it can be easily moved with the monitor and cannot be accidentally disconnected. In addition, the structure of the handle protects the alarm light from damage during transport. The alarm light assembly includes a circuit board which supports at least one light-emitting diode and a connector for supplying electrical power to the light-emitting diode(s), and a light-transmitting plastic lens which supports the circuit board. When activated, the light-emitting diodes are visible through the lens.

12 Claims, 5 Drawing Sheets

U.S. PATENT DOCUMENTS

| | | | | |
|---|---|---|---|---|
| 5,913,671 A | * | 6/1999 | Fernandez et al. | 43/18.1 |
| 5,955,956 A | * | 9/1999 | Stendahl et al. | 340/635 |
| 5,977,878 A | * | 11/1999 | Lang | 340/815.4 |
| 5,991,131 A | * | 11/1999 | Othman | 360/137 |
| 6,040,780 A | * | 3/2000 | Lucas | 340/691.1 |
| 6,135,621 A | * | 10/2000 | Bach et al. | 362/399 |
| 6,179,445 B1 | * | 1/2001 | Naoe et al. | 362/259 |
| 6,206,547 B1 | * | 3/2001 | Erlich | 362/276 |

* cited by examiner

PORTABLE PATIENT MONITOR WITH ALARM LIGHT INTEGRATED INTO HANDLE

FIELD OF THE INVENTION

This invention generally relates to portable medical diagnostic equipment. In particular, the invention relates to equipment used to monitor patients during transport in a hospital or other patient care setting.

BACKGROUND OF THE INVENTION

When providing medical care to patients, it is frequently necessary to monitor the patient using medical diagnostic instruments. One type of instrument, the patient monitor, is capable of monitoring the patient to acquire electrocardiogram data, cardiac output data, respiration data, pulse oximetry data, blood pressure data, temperature data and other parameter data. In particular, lightweight portable monitors exist which can be moved with the patient, allowing continuous monitoring during patient transport.

To facilitate monitoring at remote locations or during patient transport, modern portable patient monitors are powered by rechargeable batteries. Extended-use batteries, with quick recharge times, help maximize monitor availability. Advanced monitors have a smart battery management system which maximizes battery life, reducing maintenance and replacement. These patient monitors can also be plugged into any conventional electrical power system for use, e.g., at the patient's bedside, before and/or after the patient is transported. At the bedside, advanced patient monitors can be hardwired to a central station via a local area network (LAN) for enhanced patient surveillance efficiency. In addition, the most advanced patient monitors have a built-in wireless option which enables the monitor to go mobile without sacrificing connectivity. Such monitors also support importation of demographic and laboratory data from a hospital information system for increased efficiency.

Portable patient monitors with integral battery power supply are commercially available in a compact, ergonomic package which allows easy handling. Typically such monitors have a drop-tested rugged design which allows them to withstand the punishment of the demanding intra-hospital transport applications. Mounting options make these monitors ideally suited for headboard/footboard, siderail, rollstand and IV pole use. The compact design is achieved in part through the use of flat display panels. The color or monochrome screen accommodates all numerics and multiple waveforms.

In addition to displaying waveforms and numerics representing the data being acquired, advanced patient monitors have a central processing system which stores and analyzes the acquired data. In particular, the central processing system is programmed with algorithms for analyzing the acquired data. The central processing system controls the transfer of data to the display panel for display and to the LAN via either a hardwired or wireless connection.

A critical feature of patient monitors is the ability to provide an alarm signal in response to detection of patient parameters indicating a medical emergency. Advanced patient monitors provide patient and system status notifications having different priority levels, such as Crisis, Warning, Advisory and Message. The notification is audible and/or visual. The alarm limits are user-selectable. Previous patient monitors could not visually alert a user who was not looking at the front of the monitor. This is a serious shortcoming particularly in large hospital wards in instances where the user is out of range of the audible alarm or the audible alarm is silenced. Existing auxiliary alarm lights are typically large dome lights that communicate with the monitor by being plugged into an auxiliary alarm connector on the back of the monitor.

SUMMARY OF THE INVENTION

The present invention encompasses the integration of a means for visually indicating an alarm condition, such as an alarm light, into the handle of a portable medical diagnostic instrument, such as a patient monitor, a portable oximeter, an ambulatory device for measuring non-invasive blood pressure, devices strapped to a patient for recording ECGs over time (e.g., Holter devices), a portable $CO_2$ measuring device or an EEG device. In accordance with the preferred embodiment, an alarm light is integrated into the top of the monitor handle. Since the top of the handle is the highest point of the monitor, the alarm light can be clearly seen from the sides, top and back of the monitor. Because the alarm light is integrated into the handle structure, it can be easily moved with the monitor and cannot be accidentally disconnected. In addition, the structure of the handle protects the alarm light from damage during transport.

In accordance with the preferred embodiment of the invention, an alarm light assembly is captured between two parts of the monitor handle during assembly. This alarm light assembly comprises a circuit board which supports at least one light-emitting diode and a connector for supplying electrical power to the light-emitting diode(s), and a light-transmitting plastic lens which supports the circuit board and is captured between plastic parts of the handle. The circuit board is impaled on a plastic heat stake integrally formed as part of the lens. One or more light-emitting diodes are disposed between the lens and the circuit board. When activated, the light-emitting diodes are visible through the lens.

DETAILED DESCRIPTION OF THE PREFERRED EMBODIMENTS

Figure 1:
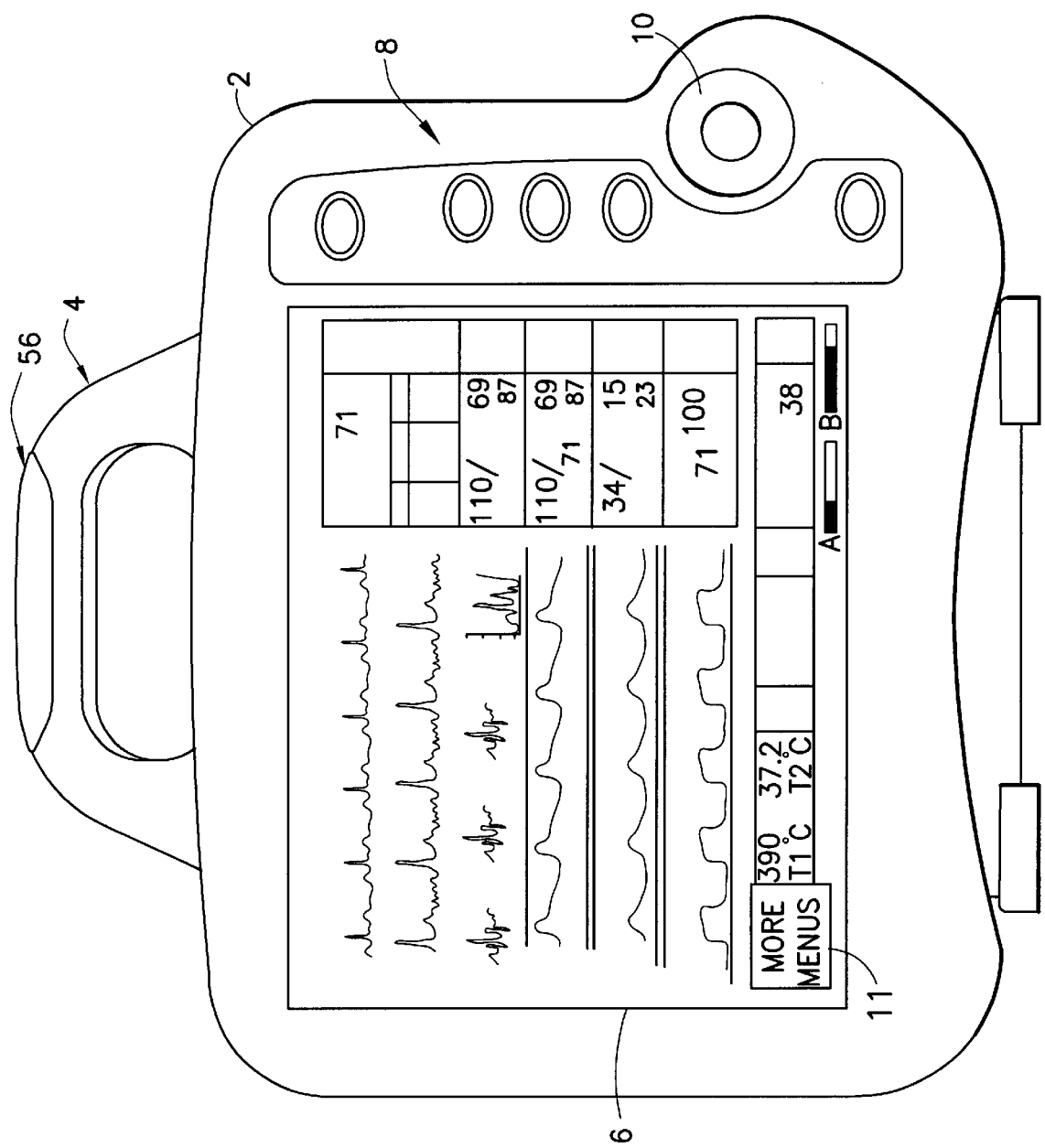
FIG. 1 is a drawing showing a generally frontal view of a portable patient monitor in accordance with the preferred embodiment of the invention.

A portable patient monitor, depicted in FIG. 1, comprises a housing 2 and a handle 4 connected to the top of the housing. Reference numeral 56 identifies a lens of an alarm light assembly, which will be described in more detail later. The monitor further comprises a flat display panel 6 secured in a generally rectangular window formed in the front face of the housing 2. An operator interface comprises a plurality of keys, forming a keypad 8, and a so-called "trim" knob 10, which allows the user to select and focus on a particular menu. The display panel 6, displays waveforms and numerical data. The status of a pair of batteries A and B is indicated in the lower right-hand corner of the display panel. A "soft" operator-actuated menu key 11, appearing in the lower left-hand corner, can be used to call up additional menus.

Figure 2:
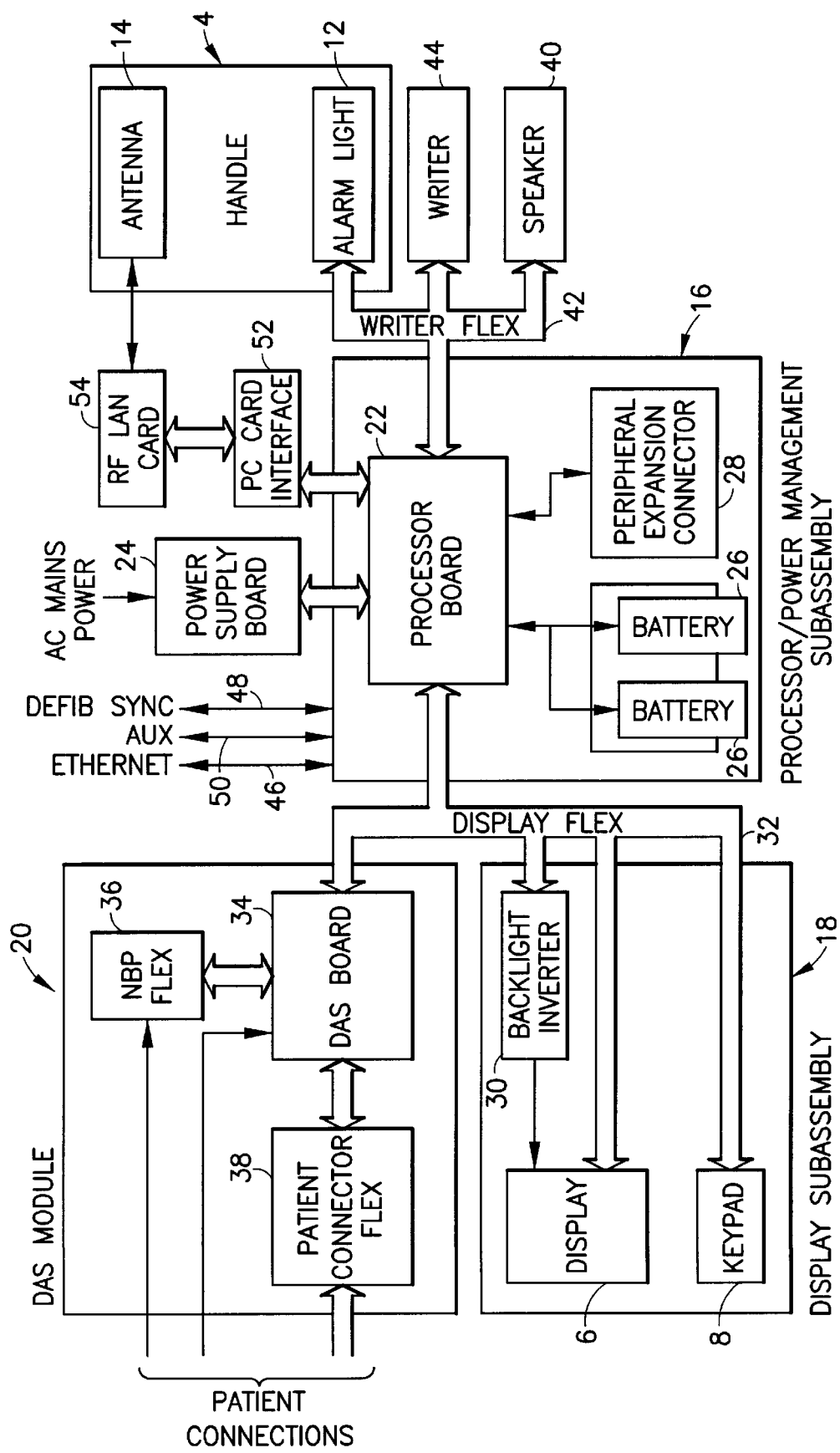
FIG. 2 is a block diagram showing a patient monitor with an alarm light integrated into the handle in accordance with the preferred embodiments of the invention.

In accordance with the preferred embodiments of the invention, an alarm light 12 is integrated into the monitor handle 4, as generally represented in the block diagram of FIG. 2. For the sake of completeness, FIG. 2 also shows the basic internal structure of the portable patient monitor depicted in FIG. 1. Although FIG. 2 also shows an antenna 14 integrated into the handle, this is the subject of a co-pending patent application.

The preferred embodiment shown in FIG. 2 comprises a processor/power management subassembly 16, a display subassembly 18 and a data acquisition system module 20, each of which will be described below.

The processor/power management subassembly 16 comprises a processor board 22 powered by an ac mains power supply via a power supply board 24. Alternatively, the processor board 22 can be powered by rechargeable batteries 26 when the patient monitor is disconnected from the mains power supply, e.g., during patient transport. The processor/power management subassembly 16 further comprises a peripheral expansion connector 28, which allows the processor to communicate with peripheral processors added as the result of future expansion of the system.

The display subassembly 18 comprises a liquid-crystal display (LCD) flat panel 6, a backlight inverter 30 for powering the fluorescent tubes of the flat display panel and a keypad 8 for operator inputs. The flat display panel 6, the backlight inverter 30 and the keypad 8 are electrically coupled to the processor board 22 via a display flexible printed circuit board (flex) 32.

The data acquisition system (DAS) module 20 comprises a plurality of ports for patient connections and a DAS board 34. The patient connection for acquiring noninvasive blood pressure (NBP) data is coupled to the DAS board 34 via an NBP flex 36. The leads for acquiring electrocardiogram (ECG), respiratory and other cardiovascular data are coupled to the DAS board 34 via a patient connector flex 38. The ECG leads connect to electrodes attached to the patient's chest. The acquired data is sent to the processor board 22 for signal processing and analysis via the display flex 32. The processor board 22 controls the display panel 6 to display the desired waveforms and numerical data based on the acquired data received from the DAS board 34.

In addition to displaying acquired data, the patient monitor depicted in FIG. 2 also has the capability of automatically activating audible and visual alarms in response to acquired data exceeding a preset alarm threshold. The alarm thresholds are user-selectable via keypad entries. The visual alarm indicator is an alarm light 12 integrated into the monitor handle 4 which flashes when activated; the audible indicator is an audio speaker 40 which emits alarm tones when activated. The alarm light 14 and audio speaker 40 are controlled by the processor board 22 via a writer flex 42. The processor board also controls a writing device 44, e.g., a thermal recorder, via the writer flex 42. The writer 44 serves to create a written record of selected data readings.

The patient monitor shown in FIG. 2 also has the ability to communicate with a LAN (not shown) via a hard-wired Ethernet connection 46, with a defibrillator (not shown) via connection 48 and with an auxiliary piece of equipment (not shown), e.g., a ventilator or a remote control device, via connection 50. The processor board provides synchronization signals to the defibrillator via connection 48. Also the patient monitor can communicate wirelessly with the LAN using an antenna 14, which is also preferably integrated into the monitor handle 4. The processor board 22 sends signals to and receives signals from the antenna 14 via a PC card interface 52 which interfaces with a RF LAN card 54. The PC card interface 52 plugs into a socket which resides on the processor board 22.

Figure 3:
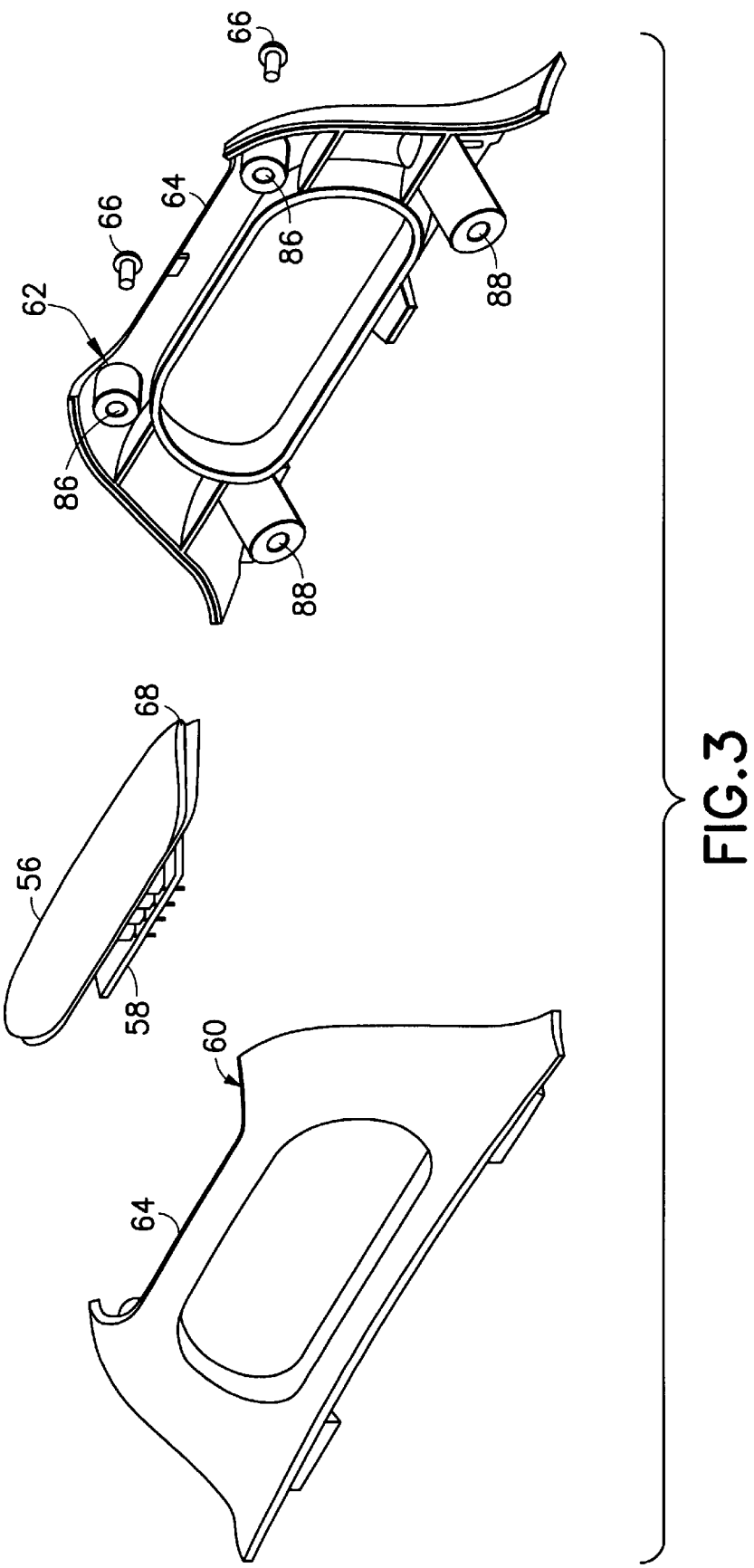
FIG. 3 is a drawing showing an exploded view of the monitor handle with integrated alarm light assembly in accordance with one preferred embodiment of the invention.
Figure 4:
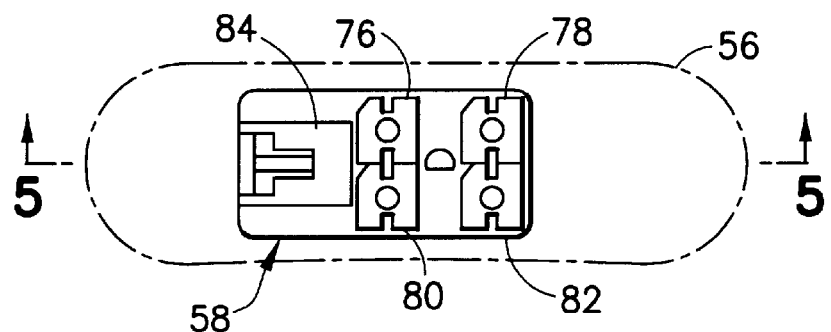
FIG. 4 is a drawing showing a top view of the circuit board of the alarm light assembly shown in FIG. 3, with the lens outlined by dashed lines.

The preferred embodiment of the present invention is shown in FIGS. 3–8. Referring to FIG. 3, the alarm light 12 is an assembly comprising a curved lens 56 made of molded plastic material and a printed circuit board 58 mounted underneath the lens 56, i.e., opposite a concave side of the lens. The convex side of the lens 56 forms part of the exterior of the handle when the latter is assembled. The internal and external surfaces of the lens are preferably textured during molding to render the clear plastic translucent.

Figure 5:
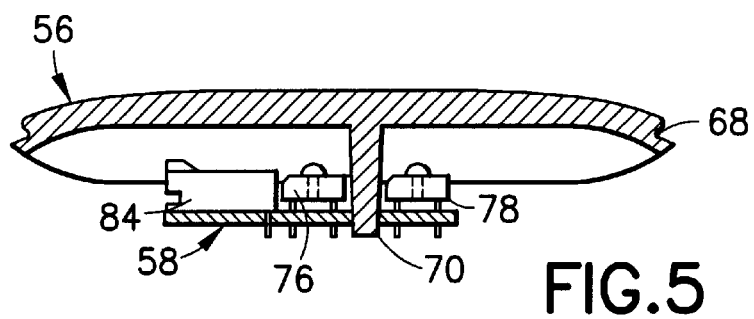
FIG. 5 is a drawing showing a sectional view of the alarm light assembly shown in FIG. 3, the section being taken along line 5—5 indicated in FIG. 4.
Figure 6:
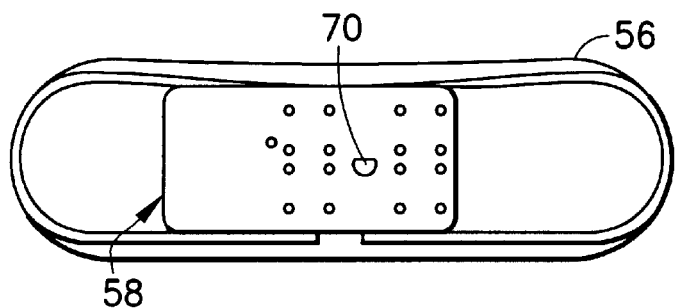
FIG. 6 is a drawing showing a bottom view of the alarm light assembly shown in FIG. 3.
Figure 7:
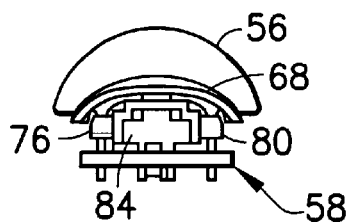
FIG. 7 is a drawing showing an end view of the alarm light assembly shown in FIG. 3.
Figure 8:
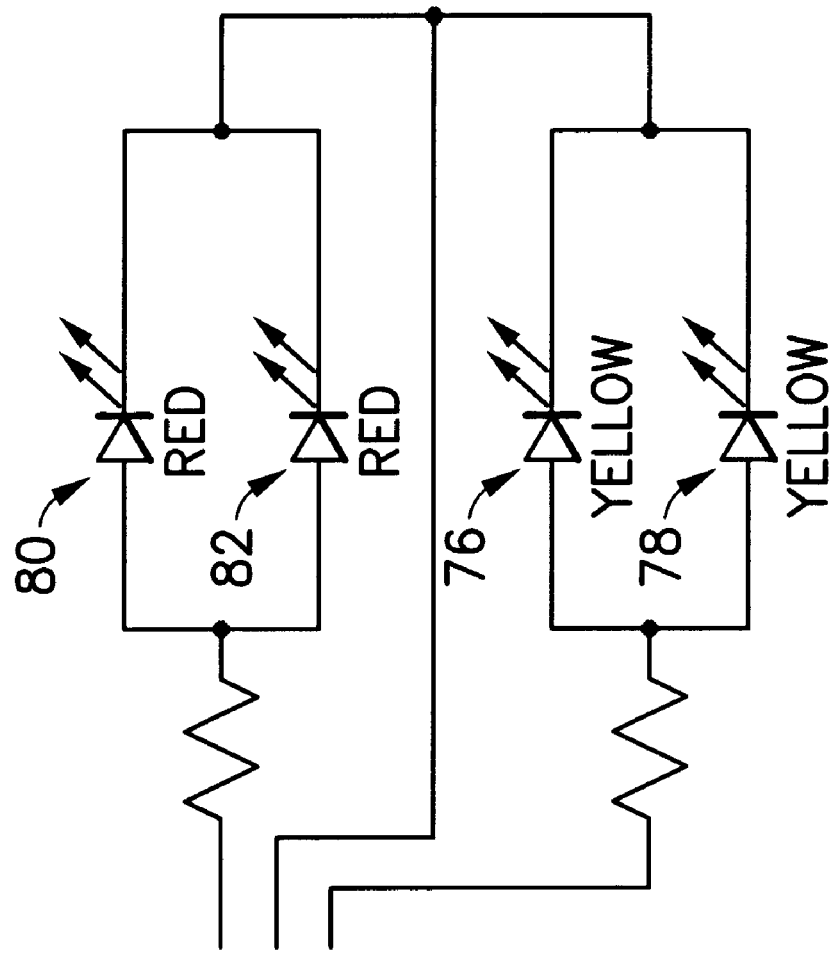
FIG. 8 is a circuit diagram showing the electrical circuitry supported by the circuit board.

In accordance with the preferred embodiment, the handle 4 comprises two molded pieces made of opaque plastic material: a front handle part 60 and a rear handle part 62. Both parts are designed with cutouts 64 which, when the two parts of the handle are fastened together by screws 66, form an opening in which the lens 56 is securely installed. Throughholes 86 are molded in the rear handle part 62 and threaded holes (not visible in FIG. 3) are molded in the front handle part 60 for receiving the screws 66. As best seen in FIGS. 5–7, a peripheral groove 68 is formed along the periphery of lens 56. When the handle is assembled, the edges of cutouts 64 engage the peripheral groove 68, thereby securely holding the alarm light assembly in place.

The handle 4 is preferably mounted at an inclined angle relative to the monitor housing, as seen in FIG. 1. In the preferred embodiment, the assembled handle is attached to the monitor housing by screws (not shown in FIG. 3). For this purpose, one pair of throughholes 88 are provided in the rear handle part 62. Another pair of throughholes (not visible in FIG. 3) are provided in the front handle part 60. The screws for attaching the handle have threaded ends which threadably engage threaded holes (not shown) in the monitor housing.

In accordance with the preferred embodiment, the printed circuit board 58 is mounted to the lens 56 via a tapered heat stake 70, which is integrally formed with the lens 56. The heat stake 70 preferably tapers linearly toward its distal end, its proximal end being integrally connected to the concave underside of the lens. Preferably the heat stake 70 is in the shape of a truncated, slightly conical rod having a planar facet formed at least along a distal section. In this case the tip of heat stake 70 has a cross-sectional shape generally defined by a circular arc having two endpoints connected by a straight line, as best seen in FIG. 6. An opening 74 (see FIG. 4) provided in the printed circuit board 58 has the same shape as the cross-sectional shape of the heat stake tip and is sized to allow a portion of the heat stake to pass through, the heat stake 70 ultimately becoming wedged in the opening 74, i.e., further penetration is stopped. The opening 74 is also oriented on the circuit board 58 so as to orient the circuit board relative to the lens 56, as seen in FIG. 6. Since the heat stake tip can enter the opening 74 only if the tip and opening are properly aligned, misalignment of the circuit board and lens during assembly is prevented. In addition, the taper of the heat stake 70 is designed so that its tip protrudes from opening 74 on the opposite side of the circuit board when the heat stake is fully inserted therein. The printed circuit board 58 is securely mounted to the lens 56 by melting the heat stake tip by the application of ultrasound energy, and then allowing the molten plastic material of the heat stake tip to fuse by cooling. As a result, a fused mass (not shown) of plastic material is formed at the tip of the heat stake 70, thereby attaching circuit board 58 to lens 56.

In accordance with the preferred embodiment, two yellow light-emitting diodes 76, 78 and two red light-emitting diodes 80, 82 are mounted on the printed circuit board 58. The light-emitting diodes are connected to the processor board (22 in FIG. 2) by means of a connector 84, which is also mounted on the printed circuit board 58. Referring to the circuit diagram of FIG. 8, the yellow light-emitting diodes 76, 78 are connected in parallel across terminals J1-2 and J1-3 of connector 84, while the red light-emitting diodes 80, 82 are connected in parallel across terminals J1-1 and J1-2 of connector 84, terminal J1-2 being connected to ground. The connector terminals in turn are electrically connected to the processor board by circuit traces on the writer flex 42, a portion of which penetrates the interior of the handle.

In accordance with the preferred embodiment, in the alarm state the yellow and red light-emitting diodes are activated in alternating sequence, e.g., during odd-numbered cycles the yellow light-emitting diodes are activated while the red light-emitting diodes are turned off, and during even-numbered cycles the red light-emitting diodes are activated while the yellow light-emitting diodes are turned off. Activation of the light-emitting diodes is controlled by the processor board in response to the acquisition of data exceeding a predetermined alarm threshold.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. For example, the person skilled in the art will readily appreciate that the number of light-emitting diodes need not be four and the number of colors need not be two. A single light-emitting diode is within the scope of the invention. Moreover, the invention is not restricted to the use of light-emitting diodes. Other light sources, e.g., subminiature light bulbs or electro-luminescent material, can also be used. In addition, while it is preferred to texturize the surfaces of the lens to render it translucent, clear (i.e., transparent) plastic material can also be utilized. In accordance with a further variation, the light source can be white while the plastic material of the lens is colored (e.g., red). Furthermore, although the handle in accordance with the preferred embodiment comprises front and rear handle parts and a lens made of light-transmitting material captured therebetween, it will be readily appreciated that the handle may comprise front and rear handle parts made of light-transmitting material with the lens eliminated. Therefore it is intended that the invention not be limited to the particular embodiment disclosed as the best mode contemplated for carrying out this invention, but that the invention will include all embodiments falling within the scope of the appended claims.

What is claimed is:

1. A portable instrument comprising:
   a housing;
   a handle attached to said housing;
   an electrically activatable source of light installed inside said handle and capable of emitting light in response to an activation signal;
   a data acquisition system located within said housing; and
   a processor located within said housing and coupled to receive acquired data from said data acquisition system, said processor being capable of detecting if said acquired data satisfies a predetermined alarm condition and issuing said activation signal to said source of light in response to detection of said predetermined alarm conditions,
   wherein said handle comprises a lens made of light-transmitting material, said lens having a groove along its periphery, and further comprises front and rear handle parts, each of said front and rear handle parts having an edge which engages said groove, thereby holding said lens.

2. The portable instrument as recited in claim 1, wherein said handle further comprises a support structure that supports said source of light in a position beneath said lens, said support structure depending from said lens.

3. The portable instrument as recited in claim 2, wherein said support structure is integrally formed with said lens and made of said light-transmitting material.

4. The portable instrument as recited in claim 2, further comprising a circuit board arranged inside said handle and suspended from said lens by means of said support structure with no support along its periphery, wherein said support structure comprises a stake which penetrates and supports said circuit board and said source of light is mounted on said circuit board.

5. The portable instrument as recited in claim 1, wherein said lens is translucent.

6. The portable instrument as recited in claim 1, wherein said source of light comprises a light-emitting diode.

7. The portable instrument as recited in claim 1, further comprising a circuit board arranged inside said handle, wherein said lens comprises a stake which penetrates and supports said circuit board and said source of light is mounted on said circuit board.

8. The portable instrument as recited in claim 7, wherein said stake comprises a section having a cross section of predetermined shape, and said circuit board comprises an opening having said same predetermined shape, said section of said stake being able to penetrate said opening only when said circuit board has a predetermined orientation relative to said lens.

9. The portable instrument as recited in claim 7, wherein said stake comprises a section which penetrates an opening in said circuit board and a mass at a tip of said stake, said mass being unable to penetrate said opening in said circuit board.

10. The portable instrument as recited in claim 9, wherein said stake is made of a material which can be rendered molten by application of ultrasound energy.

11. The portable instrument as recited in claim 1, further comprising a battery for supplying electrical power to said processor.

12. The portable instrument as recited in claim 1, further comprising a flexible printed circuit for electrically coupling said processor to said source of light.

* * * * *